United States Patent
Pullagurla et al.

(10) Patent No.: US 10,626,076 B2
(45) Date of Patent: Apr. 21, 2020

(54) PROCESS FOR THE SYNTHESIS OF DIMETHYL FUMARATE

(71) Applicant: BIOPHORE INDIA PHARMACEUTICALS PVT. LTD., Hyderabad (IN)

(72) Inventors: Manik Reddy Pullagurla, Hyderabad (IN); Jagadeesh Babu Rangisetty, Hyderabad (IN); Mecheril Valsan Nandakumar, Hyderabad (IN); Nagarapu Radha, Hyderabad (IN)

(73) Assignee: BIOPHORE INDIA PHARMAEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 15/126,526

(22) PCT Filed: Dec. 29, 2014

(86) PCT No.: PCT/IN2014/050007
§ 371 (c)(1),
(2) Date: Sep. 15, 2016

(87) PCT Pub. No.: WO2015/140811
PCT Pub. Date: Sep. 24, 2015

(65) Prior Publication Data
US 2017/0096384 A1    Apr. 6, 2017

(30) Foreign Application Priority Data

Mar. 17, 2014   (IN) ............................ 1400/CHE/2014

(51) Int. Cl.
*C07C 67/08* (2006.01)
*C07C 67/333* (2006.01)
*C07C 67/14* (2006.01)

(52) U.S. Cl.
CPC .............. *C07C 67/08* (2013.01); *C07C 67/14* (2013.01); *C07C 67/333* (2013.01)

(58) Field of Classification Search
None
See application file for complete search history.

(56) References Cited

U.S. PATENT DOCUMENTS 2,653,168 A * 9/1953 Spatz ...................... C07C 51/60
562/853

FOREIGN PATENT DOCUMENTS

| WO | WO 2012/170923 | 12/2012 | |
| WO | WO 2012170923 | * | 12/2012 |

OTHER PUBLICATIONS

Dymicky ("Preparation of Monomethyl Fumarate" Organic Preparations and Procedures Int. 15(4), 1983, p. 233-238).*
Campbell ("Some New Fumaric Acid Derivatives. Preparation of Mixed Fumarates and Thiolfumarates" J. Org. Chem. 26(3), 1961, p. 697-700).*
Jaeger ("Regioselectivity of Diels-Alder Reactions of a Surfactant 1,3-Diene with Surfactant Dienophiles" J. Org. Chem, 1993, 58 p. 6745-6755) (Year: 1993).*
Papadopoulou ("Dimethyl fumarate for multiple sclerosis" Expert Opinion on Investigational Drugs, 19:12, 2010, p. 1603-1612) Year: 2010).*

* cited by examiner

*Primary Examiner* — Amy C Bonaparte
(74) *Attorney, Agent, or Firm* — Seyfarth Shaw LLP

(57) ABSTRACT

The present invention describes an improved process for the industrial scale production of dimethyl fumarate. The process involves a one-pot ring opening reaction of maleic anhydride to monomethyl maleate and isomerization into the corresponding monomethyl fumarate in presence of a Lewis acid. Finally the mono methyl fumarate was converted into the dimethyl fumarate by an acid catalyzed esterification reaction.

3 Claims, No Drawings

PROCESS FOR THE SYNTHESIS OF DIMETHYL FUMARATE

FIELD OF THE INVENTION

The invention relates to an improved process for the preparation of dimethyl fumarate (I) in a substantially pure form used in the treatment of multiple sclerosis.

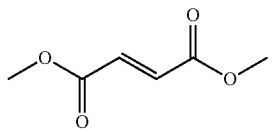

Formula I

The invention also provides a one pot process for the preparation of monomethyl fumarate. The obtained monomethyl fumarate is further converted in to dimethyl fumarate.

BACKGROUND OF THE INVENTION

Dimethyl fumarate, a dimethyl ester of fumaric acid is chemically known as dimethyl (E) butenedioate. It is marketed under the trade name Tecfidera by Biogene and is a FDA approved drug for the treatment of multiple sclerosis. Dimethyl fumarate has also found applications in organ transplant treatment to reduce or suppress the rejection by the recipient.

General synthetic approach reported for the production of dimethyl fumarate involves the esterification of fumaric acid to the diester in presence of an acid catalyst. WO 2012/170923 describes the synthesis of the dimethyl fumarate by the sulphuric acid catalyzed esterification of fumaric acid. However, the esterification of fumaric acid in presence of sulphuric acid and methanol generates dimethyl sulphate as the by-product, which is a known genotoxic impurity.

Other methods reported for the synthesis of dimethyl fumarate are by the isomerization of the dimethyl maleate using different catalyst such as fumaryl chloride, triphenyl phosphine, thiourea, transition metal catalyst etc.

Most of the reported procedures are not suitable for the commercial scale production of dimethyl fumarate. In order to overcome the problems associated with prior art, there is a need to develop an efficient and cost effective method for the commercial scale production of dimethyl fumarate.

OBJECTS OF THE INVENTION

One object of the invention is to provide an efficient and industrially viable process for the preparation of dimethyl fumarate.

Another object of the invention is to provide a one pot process for the preparation of monomethyl fumarate.

SUMMARY OF THE INVENTION

Accordingly, the present invention provides a novel process for preparation of dimethyl fumarate of formula I.

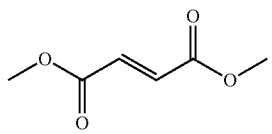

Formula I

In general embodiment, the invention comprises two steps. The first step of the invention comprises a novel one pot process for synthesis of monomethyl fumarate without isolating monomethyl maleate intermediate and hence avoiding the use of large quantities of solvents at a commercial scale.

In the next step, the monomethyl maleate is converted into dimethyl fumarate.

The invention summarized below is further described in the following paragraphs and by following examples.

The preferred embodiments of the invention provide a novel process for the preparation of dimethyl fumarate of formula I comprising the steps of:
i. a one pot ring opening reaction of maleic anhydride using methanol to obtain monomethyl maleate, followed by Lewis acid catalyzed isomerization of the monomethyl maleate to obtain monomethyl fumarate;
ii. conversion of monomethyl fumarate into the dimethyl fumarate by an acid chloride mediated esterification.

The Lewis acid employed in step (i) may be selected from $AlCl_3$, $ZnCl_2$, $SnCl_4$ and $TiCl_4$.

The acid chloride employed in step (ii) may be selected from thionyl chloride, oxalyl chloride and pivoloyl chloride.

The intermediary monomethyl maleate obtained in step (i) is not isolated from the reaction process and is further proceeded for Lewis acid catalyzed isomerization to obtain the monomethyl fumarate.

DETAILED DESCRIPTION OF THE INVENTION

The invention relates to a process for the synthesis of dimethyl fumarate of formula I, which comprises a one pot ring opening reaction of maleic anhydride using methanol to obtain monomethyl maleate followed by the Lewis acid catalyzed isomerization of the intermediate to the monomethyl fumarate.

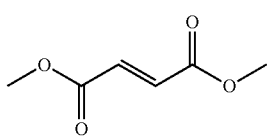

Formula I

The ring opening of the maleic anhydride with methanol can be carried out at 25 to 60° C. and the quantity of methanol can be used ranging from 0.5 to 2 equivalents.

In another aspect of the invention, the catalyst used for the isomerization of monomethyl maleate to monomethyl fumarate is a Lewis acid. The Lewis acid, which can be employed is $AlCl_3$, $ZnCl_2$, $SnCl_4$, $TiCl_4$ or the like. The quantity of Lewis acid used for the isomerization may be varied from catalytic to stoichiometric amount. The temperature of the reaction may be varied from 25 to 100° C.

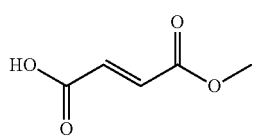

Mono methyl fumarate

In yet another aspect of the invention, the monomethyl fumarate is converted in to the dimethyl fumarate by converting it to its acid chloride in an organic solvent. The reagent used for the acid chloride conversion is selected from the group comprising of thionyl chloride, oxalyl chloride, pivoloyl chloride or the like. The solvent used for the conversion of acid chloride is selected from the group consisting of alcohols like methanol, propanol, butanol or the like, hydrocarbons like $CH_2Cl_2$, Toluene, Hexane or the like, ethers like THF, MTBE or the like. The acid chloride is isolated and later quenched into methanol which generates the dimethylfumarate. The temperature of the reaction may vary between 25 to 100° C.

The process is particularly advantageous that there is no formation of dimethyl sulfate impurity which is genotoxic and has to be controlled in the API in the prior art processes.

The dimethyl fumarate obtained by this process is completely synthetic and avoids the use of fumaric acid starting material which could be obtained from non-synthetic sources.

The process of the invention is illustrated in the following Scheme.

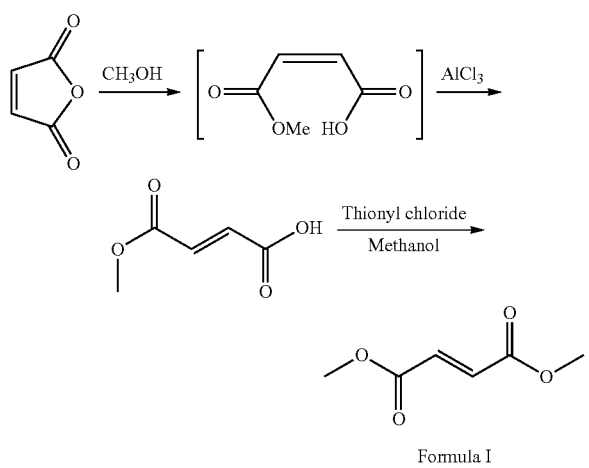

Formula I

In conclusion, the authors have disclosed an improved industrial scale process for the synthesis of dimethyl fumarate.

Preparation of Monomethyl Fumarate 100 g of Maleic anhydride was dissolved in 0.4 L, of methanol and the reaction mass was stirred for 3-4 hrs at 45-50° C. To the reaction mass, 150 ml of ethyl acetate was added and 10.0 g of anhydrous aluminum chloride was added at 45-50° C. for 10-20 min and maintained the reaction mass for 4-5 hrs at 70-75° C. After completion of reaction, the reaction mixture was maintained for 60-80 minutes at 5-10° C. and filtered. The solid obtained was washed with chilled ethyl acetate and dried. 80% of the product was isolated after purification.

Preparation of Monomethyl Fumarate 100 g of Maleic anhydride was dissolved in 0.4 L, of methanol and stirred the reaction mass for 3-4 hrs at 45-50° C. To the reaction mass, 10.0 g of anhydrous aluminum chloride was added at 45-50° C. for 10-20 min and 150 ml of toluene was added and maintained the reaction mass for 4-5 hrs at 70-75° C. After completion of reaction, the reaction mixture was maintained for 60-80 minutes at 5-10° C. and filtered. The solid obtained was washed with chilled toluene and dried. 80% of the product was isolated after purification.

Preparation of Dimethyl Fumarate 100 g of Monomethyl fumarate was dissolved in 500 ml of methanol and cooled to 10° C. 15 ml of thionyl chloride was slowly added to the reaction mass for 40-60 min and the reaction mass was heated to 60-65° C. and maintained for 10-12 h. After completion of the reaction the product was isolated and purified in methanol and water to yield 80 g of dimethyl fumarate with required spec.

We claim:

1. A improved process for the preparation of dimethyl fumarate comprising:
   (i) a ring opening reaction of maleic anhydride using methanol to obtain monomethyl maleate, followed by Lewis acid catalyzed isomerization of the monomethyl maleate to obtain monomethyl fumarate;
   (ii) conversion of monomethyl fumarate into dimethyl fumarate by an acid chloride mediated esterification, characterized in that the acid chloride mediated esterification comprises the following steps:
   a. dissolving monomethyl fumarate obtained in step (i) in methanol;
   b. adding thionyl chloride to the solution obtained in step (a);
   c. heating the reaction mixture obtained in step (b) at 60-65° C. for 10-12 hours; and
   d. isolating dimethyl fumarate;
   wherein the acid chloride mediated esterification is carried out in the absence of base and avoids separate formation of crude monomethyl fumaryl chloride.

2. The process according to claim 1, wherein the Lewis acid employed in step (i) is selected from the group consisting of $AlCl_3$, $ZnCl_2$, $SnCl_4$ and $TiCl_4$.

3. The process according to claim 1, wherein the step (i) is completed without isolation of the intermediary monomethyl maleate.

* * * * *